United States Patent
Kangas et al.

(10) Patent No.: US 11,484,320 B2
(45) Date of Patent: Nov. 1, 2022

(54) LEFT ATRIAL APPENDAGE CLOSURE DEVICE WITH ANTI-THROMBOGENIC COVERING

(71) Applicant: BOSTON SCIENTIFIC SCIMED, INC., Maple Grove, MN (US)

(72) Inventors: Steven L. Kangas, Woodbury, MN (US); Edward Kopesky, Mahtomedi, MN (US); Yen-Lane Chen, New Brighton, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 17/125,747

(22) Filed: Dec. 17, 2020

(65) Prior Publication Data
US 2021/0186516 A1 Jun. 24, 2021

Related U.S. Application Data

(60) Provisional application No. 62/949,976, filed on Dec. 18, 2019.

(51) Int. Cl.
*A61B 17/12* (2006.01)
*A61L 33/00* (2006.01)

(52) U.S. Cl.
CPC .. *A61B 17/12122* (2013.01); *A61B 17/12031* (2013.01); *A61B 17/12172* (2013.01);
(Continued)

(58) Field of Classification Search
CPC ........ A61B 17/12122; A61B 17/12031; A61B 17/12172; A61B 17/12177;
(Continued)

(56) References Cited

U.S. PATENT DOCUMENTS

| 2006/0173492 A1 | 8/2006 | Akerfeldt et al. |
| 2014/0135817 A1* | 5/2014 | Tischler ........... A61B 17/12172 29/428 |
| 2015/0005809 A1 | 1/2015 | Ayres et al. |

FOREIGN PATENT DOCUMENTS

| EP | 1469790 A2 | 8/2003 |
| EP | 1523957 A2 | 4/2005 |

(Continued)

OTHER PUBLICATIONS

Capodanno et al., Properties and Clinical Development of a Novel Coating Technology: The ply[bis(trifluoroethoxy) phosphazene], Recent Patents on Drug Delivery & Formulations, vol. 4, No. 1, pp. 18-22, 2010.

(Continued)

*Primary Examiner* — Katherine M Shi
*Assistant Examiner* — Paige A Codrington
(74) *Attorney, Agent, or Firm* — Seager, Tufte & Wickhem LLP

(57) ABSTRACT

Medical devices as wells as methods for making and using medical devices are disclosed. An example medical device may include a left atrial appendage device. The left atrial appendage device may include an expandable frame configured to shift between a first configuration and an expanded configuration. A fabric mesh may be disposed along at least a portion of the expandable frame. An anti-thrombogenic coating may be disposed along the fabric mesh.

17 Claims, 6 Drawing Sheets

(52) U.S. Cl.
CPC ..... *A61B 17/12177* (2013.01); *A61L 33/0005* (2013.01); *A61L 2430/36* (2013.01)

(58) Field of Classification Search
CPC .. A61B 2017/00893; A61B 2017/3966; A61L 2430/36; A61L 33/0005; A61L 33/064; A61L 31/06; A61L 31/10; A61L 31/146; A61L 31/16; A61L 31/14
USPC .......................................................... 606/200
See application file for complete search history.

(56) References Cited

FOREIGN PATENT DOCUMENTS

| EP | 1759724 A1 | 3/2007 | |
|----|------------|--------|---|
| EP | 3328396 A1 | 2/2017 | |
| EP | 3426181 A1 | 9/2017 | |
| EP | 3733095 A1 * | 11/2020 | ......... A61B 17/0057 |

OTHER PUBLICATIONS

International Search Report and Written Opinion dated Mar. 23, 2021 for International Application No. PCT/US2020/065721.

\* cited by examiner

LEFT ATRIAL APPENDAGE CLOSURE DEVICE WITH ANTI-THROMBOGENIC COVERING

CROSS-REFERENCE TO RELATED APPLICATIONS

This application claims the benefit of priority under 35 U.S.C. § 119 to U.S. Provisional Application Ser. No. 62/949,976, filed Dec. 18, 2019, the entirety of which is incorporated herein by reference.

TECHNICAL FIELD

The present disclosure pertains to medical devices, and methods for manufacturing medical devices. More particularly, the present disclosure pertains to occlusive devices such as those deployed adjacent to the left atrial appendage.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. A left atrial appendage device is disclosed. The left atrial appendage device comprises: an expandable frame configured to shift between a first configuration and an expanded configuration; a fabric mesh disposed along at least a portion of the expandable frame; and an anti-thrombogenic coating disposed along the fabric mesh.

Alternatively or additionally to any of the embodiments above, the fabric mesh includes a plurality of filaments.

Alternatively or additionally to any of the embodiments above, the plurality of filaments include polyethylene terephthalate.

Alternatively or additionally to any of the embodiments above, the plurality of filaments include polyester.

Alternatively or additionally to any of the embodiments above, the anti-thrombogenic coating encapsulates at least some of the plurality of filaments.

Alternatively or additionally to any of the embodiments above, the anti-thrombogenic coating individually coats each of the plurality of filaments.

Alternatively or additionally to any of the embodiments above, the plurality of filaments are arranged as non-woven configuration.

Alternatively or additionally to any of the embodiments above, the plurality of filaments are arranged into a fiber bundle.

Alternatively or additionally to any of the embodiments above, the anti-thrombogenic coating migrates to an interior region of the fiber bundle.

Alternatively or additionally to any of the embodiments above, the anti-thrombogenic coating includes a fluoropolymer.

Alternatively or additionally to any of the embodiments above, the anti-thrombogenic coating includes polyvinylidene fluoride.

Alternatively or additionally to any of the embodiments above, the anti-thrombogenic coating includes a polyvinylidene fluoride copolymer.

Alternatively or additionally to any of the embodiments above, the anti-thrombogenic coating includes poly(vinylidene fluoride-co-hexafluoropropylene).

Alternatively or additionally to any of the embodiments above, the anti-thrombogenic coating includes poly[bis (trifluoroethoxy)phosphazene].

A left atrial appendage device is disclosed. The left atrial appendage device comprises: an expandable framework configured to shift between a delivery configuration and a deployed configuration; wherein the expandable framework is configured to engage a left atrial appendage when in the deployed configuration; a fabric disposed along at least a portion of the expandable framework, the fabric including one or more knitted fiber bundles; wherein each of the one or more knitted fiber bundles include a plurality of filaments; and an anti-thrombogenic coating disposed along each of the plurality of filaments.

Alternatively or additionally to any of the embodiments above, the anti-thrombogenic coating encapsulates each of the plurality of filaments.

Alternatively or additionally to any of the embodiments above, the anti-thrombogenic coating includes a fluoropolymer.

Alternatively or additionally to any of the embodiments above, the anti-thrombogenic coating includes poly(vinylidene fluoride-co-hexafluoropropylene).

An occlusive medical device is disclosed. The occlusive medical device comprises: an expandable frame configured to shift between a delivery configuration and an expanded configuration; wherein the expandable frame is configured to be implanted adjacent to a left atrial appendage; a fabric mesh disposed along at least a portion of the expandable frame, the fabric mesh including one or more fiber bundles arranged into a pattern; wherein each of the one or more fiber bundles include a plurality of filaments; an anti-thrombogenic coating disposed along each of the plurality of filaments; and wherein at least one of the one or more fiber bundles includes an interior region and wherein a section of the anti-thrombogenic coating is disposed along the interior region.

Alternatively or additionally to any of the embodiments above, the anti-thrombogenic coating encapsulates each of the plurality of filaments.

A left atrial appendage device is disclosed. The left atrial appendage device comprises: an expandable frame configured to shift between a first configuration and an expanded configuration; a fabric mesh disposed along at least a portion of the expandable frame; and an anti-thrombogenic coating disposed along the fabric mesh and along the expandable frame.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
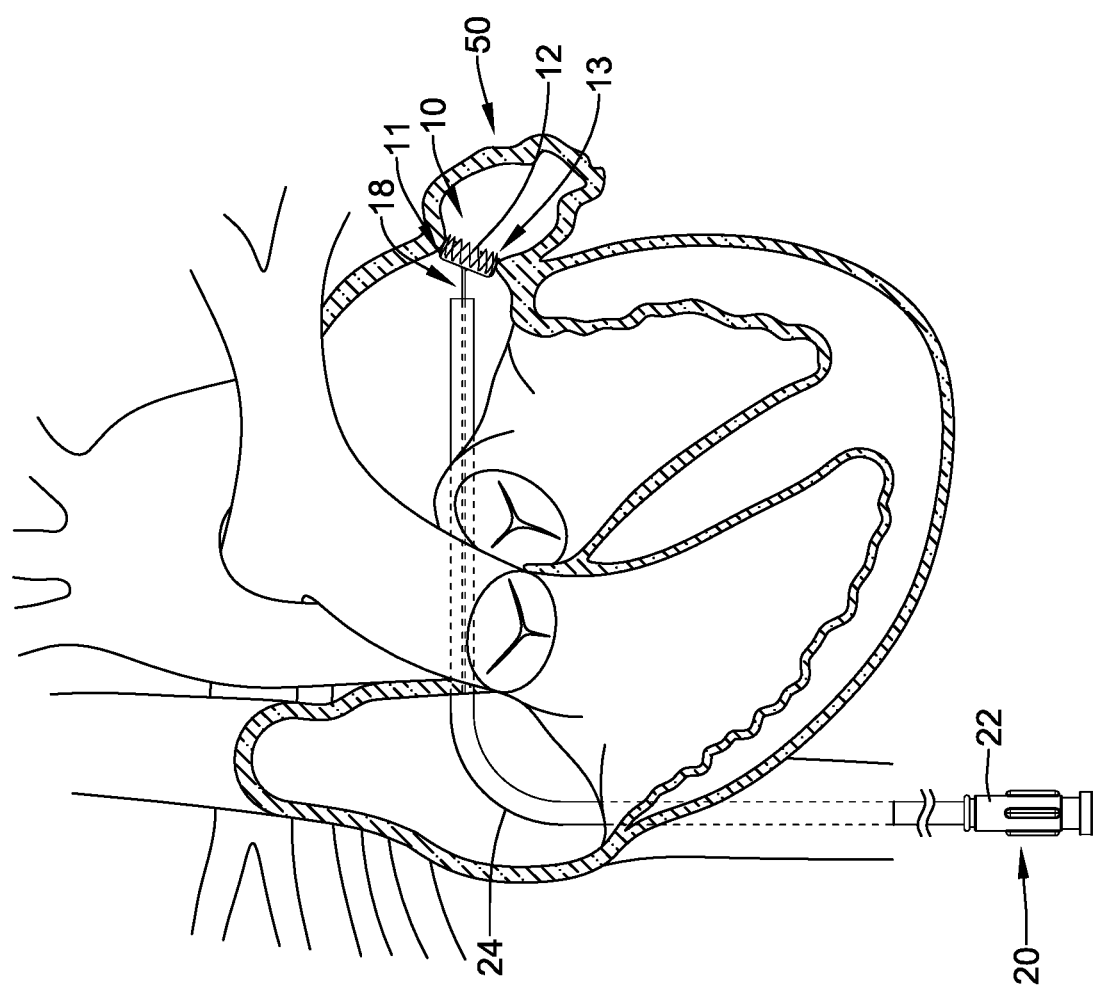
FIG. 1 is a plan view of an example medical device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

The left atrial appendage (LAA) is a small sac attached to the left atrium of the heart as a pouch-like extension. In patients suffering from atrial fibrillation, the left atrial appendage may not properly contract with the left atrium, causing stagnant blood to pool within its interior, which can lead to the undesirable formation of thrombi within the left atrial appendage. Thrombi forming in the left atrial appendage may break loose from this area and enter the blood stream. Thrombi that migrate through the blood vessels may eventually plug a smaller vessel downstream and thereby contribute to stroke. Clinical studies have shown that the majority of blood clots in patients with atrial fibrillation are found in the left atrial appendage. As a treatment, medical devices have been developed which are positioned in the left atrial appendage and deployed to close off the ostium of the left atrial appendage. Over time, the exposed surface(s) spanning the ostium of the left atrial appendage becomes covered with tissue (a process called endothelization), effectively removing the left atrial appendage from the circulatory system and reducing or eliminating the number of thrombi which may enter the blood stream from the left atrial appendage. In an effort to reduce the occurrence of thrombi formation within the left atrial appendage and prevent thrombi from entering the blood stream from within the left atrial appendage, it may be desirable to develop medical devices and/or occlusive implants that close off the left atrial appendage from the heart and/or circulatory system, thereby lowering the risk of stroke due to thrombolytic material entering the blood stream from the left atrial appendage. Example medical devices and/or occlusive implants which seal the left atrial appendage (or other similar openings) are disclosed herein.

FIG. 1 illustrates an example occlusive implant 10 (e.g., a left atrial appendage medical device) positioned within the left atrial appendage 50. FIG. 1 further illustrates that the occlusive implant 10 may be inserted and advanced through a body lumen via an occlusive implant delivery system 20. In some instances, an occlusive implant delivery system 20 may include a delivery catheter 24 which is guided toward the left atrium via various chambers and lumens of the heart (e.g., the inferior vena cava, superior vena cava, the right atrium, etc.) to a position adjacent the left atrial appendage 50.

The delivery system 20 may include a hub 22. The hub 22 may be manipulated by a clinician to direct the distal end region of the delivery catheter 24 to a position adjacent the left atrial appendage 50. In some instances, an occlusive implant delivery system 20 may include a core wire 18. Further, a proximal end region 11 of the occlusive implant 10 may be configured to releasably attach, join, couple, engage, or otherwise connect to the distal end of the core wire 18. In some instances, the proximal end region 11 of the occlusive implant 10 may include a threaded insert coupled thereto. In some instances, the threaded insert may be configured to and/or adapted to couple with, join to, mate with, or otherwise engage a threaded member disposed at the distal end of a core wire 18. Other structures for releasably coupling and/or engaging the proximal end of the occlusive implant 10 to the distal end of the core wire 18 are also contemplated.

FIG. 1 further illustrates the occlusive implant 10 positioned adjacent the left atrial appendage 50 via the delivery catheter 24 (described above). It can be appreciated that in some examples, the occlusive implant 10 may be configured to shift between a first or collapsed configuration and a second or expanded configuration. For example, in some instances, the occlusive implant 10 may be in a collapsed configuration during delivery via the occlusive implant delivery system 20, whereby the occlusive implant 10 expands to an expanded configuration once deployed from the occlusion implant delivery system 20.

Additionally, FIG. 1 illustrates that the occlusive implant 10 may include an expandable frame or framework 12. The expandable framework 12 may be compliant and, therefore, substantially conform to and/or be in sealing engagement with the shape and/or geometry of a lateral wall of a left atrial appendage 50 in the expanded configuration. In some embodiments, the occlusive implant 10 may expand to a size, extent, or shape less than or different from a maximum unconstrained extent, as determined by the surrounding tissue and/or lateral wall of the left atrial appendage 50. Further, it can be appreciated that the elements of the expandable framework 12 may be tailored to increase the flexibility of the expandable framework 12 and/or the occlusive implant 10, thereby permitting the expandable framework 12 and/or the occlusive implant 10 to conform to the tissue around it, rather than forcing the tissue to conform to the expandable framework 12 and/or the occlusive implant 10. Additionally, in some instances, it may be desirable to design the occlusive implant 10 to include various features, components and/or configurations which improve the sealing capabilities of the occlusive implant 10 within the left atrial appendage.

FIG. 1 illustrates that the distal end region 13 of the expandable framework 12 may extend farther into the left atrial appendage 50 as compared to the proximal end region 11 of the expandable framework 12. It can be appreciated that as the expandable framework 12 is advanced into the left atrial appendage 50, the distal end region 13 may engage with tissue defining the left atrial appendage 50. In other words, in some examples the distal end region 13 may be considered the "leading" region of the expandable framework 12 as it enters into the left atrial appendage 50. However, this is not intended to be limiting. Rather, in some examples the proximal end region 11 may be considered the "leading" region of the expandable framework 12 as it enters into the left atrial appendage 50.

Figure 2:
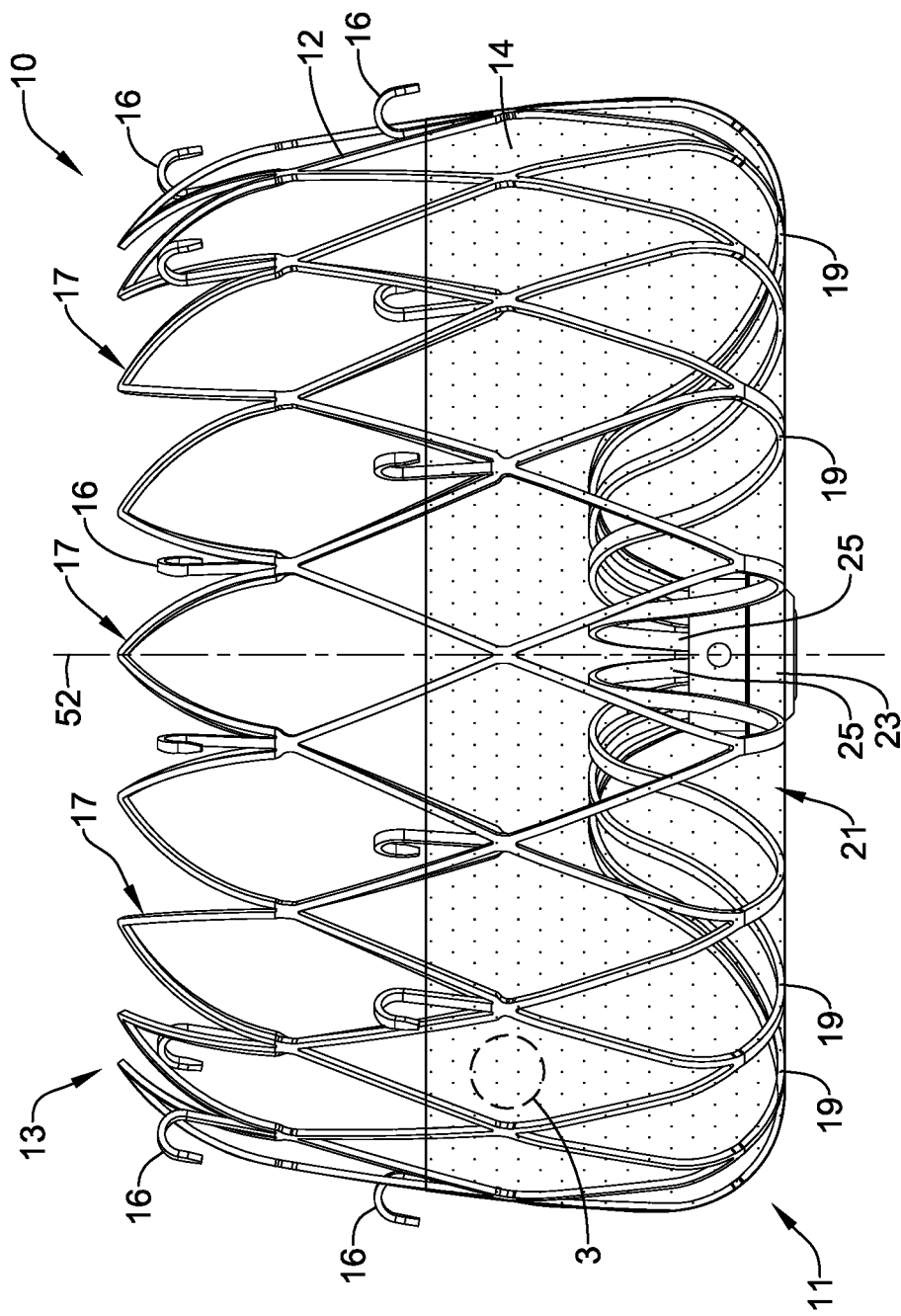
FIG. 2 is a perspective view of an example medical device.

FIG. 2 illustrates an example occlusive implant 10. The occlusive implant 10 may include an expandable framework 12. The expandable framework 12 may include a proximal end region 11 and a distal end region 13. FIG. 2 further illustrates that the expandable framework 12 may include one or more projections 17 extending in a proximal-to-distal direction. In some instances (such as that shown in FIG. 2), plurality of projections 17 may extend circumferentially around a longitudinal axis 52 of the expandable framework 12. In other words, in some examples the projections 17 may resemble the peaks of a "crown" extending circumferentially around a longitudinal axis 52 of the expandable framework 12. While the above discussion (and the illustration shown in FIG. 2), shows a plurality of projections 17, it is contemplated that the occlusive implant 10 may include 1, 2, 3, 4, 5, 6, 7, 8, 9, 10, 11, 12 or more individual projections 17 disposed in a variety of arrangements along the expandable framework 12.

Additionally, FIG. 2 illustrates that the proximal end region 11 of the expandable framework 12 may include a plurality of support members 19 extending circumferentially around the longitudinal axis 52 of the expandable framework 12. FIG. 2 illustrates that that plurality of support members 19 may include one or more curved portions which are shaped such that they define a "recess" 21 extending distally into the expandable framework 12. As illustrated in FIG. 2, the recess 21 may extend circumferentially around the longitudinal axis 52. Further, FIG. 2 illustrates that each of the plurality of support members 19 may include a first end 25 which is attached to a central hub 23. It can be appreciated that the central hub 23 may be aligned along the longitudinal axis 52 of the expandable framework 12. As will be described in greater detail below, FIG. 2 illustrates that the hub 23 may be positioned such that it lies within the recess 21 defined by the plurality of support members 19.

The occlusive implant 10 may also include an occlusive member 14 disposed on, disposed over, disposed about, or covering at least a portion of the expandable framework 12. In some instances, the occlusive member 14 may be disposed on, disposed over, disposed about or cover at least a portion of an outer (or outwardly-facing) surface of the expandable framework 12. FIG. 2 further illustrates that the occlusive member 14 may extend only partially along the longitudinal extent of the expandable framework 12. However, this is not intended to be limiting. Rather, the occlusive member 14 may extend along the longitudinal extent of the expandable framework 12 to any degree (e.g., the full longitudinal extend of the expandable framework 12).

In some embodiments, the occlusive member 14 may be permeable or impermeable to blood and/or other fluids, such as water. In some embodiments, the occlusive member 14 may include a woven fabric/material or mesh, a non-woven fabric/material or mesh, a braided and/or knitted material, a fiber, a sheet-like material, a fabric, a mesh, a fabric mesh, a polymeric membrane, a metallic or polymeric mesh, a porous filter-like material, a covering, and/or other suitable construction. In some embodiments, the occlusive member 14 may prevent thrombi (i.e. blood clots, etc.) from passing through the occlusive member 14 and out of the left atrial appendage into the blood stream. In some embodiments, the occlusive member 14 may promote endothelialization after implantation, thereby effectively removing the left atrial appendage from the patient's circulatory system. Some suitable, but non-limiting, examples of materials for the occlusive member 14 are discussed below.

FIG. 2 further illustrates that the expandable framework 12 may include a plurality of anchor members 16 disposed about a periphery of the expandable framework 12. The plurality of anchor members 16 may extend radially outward from the expandable framework 12. In some embodiments, at least some of the plurality of anchor members 16 may each have and/or include a body portion and a tip portion projecting circumferentially therefrom, as shown in FIG. 2. Some suitable, but non-limiting, examples of materials for the expandable framework 12 and/or the plurality of anchor members 16 are discussed below.

In some examples, the expandable framework 12 and the plurality of anchor members 16 may be integrally formed and/or cut from a unitary member. In some embodiments, the expandable framework 12 and the plurality of anchor members 16 may be integrally formed and/or cut from a unitary tubular member and subsequently formed and/or heat set to a desired shape in the expanded configuration. In some embodiments, the expandable framework 12 and the plurality of anchor members 16 may be integrally formed and/or cut from a unitary flat member, and then rolled or formed into a tubular structure and subsequently formed and/or heat set to the desired shape in the expanded configuration. Some exemplary means and/or methods of making and/or forming the expandable framework 12 include laser cutting, machining, punching, stamping, electro discharge machining (EDM), chemical dissolution, etc. Other means and/or methods are also contemplated.

As illustrated in FIG. 2, the plurality of anchor members 16 disposed along the expandable framework 12 may include two rows of anchor members 16. However, this is not intended to be limiting. Rather, the expandable framework 12 may include a single row of anchor members 16. In other examples, the expandable framework 12 may include more than two rows of anchor members 16. For example, in some instances the expandable framework 12 may include 1, 2, 3, 4 or more rows of anchor members 16.

While FIG. 2 illustrates an expandable framework 12 which may be formed from a unitary member, this is not intended to be limiting. Rather, it is contemplated the expandable framework 12 may include a variety of different configurations which may be formed via a variety of manufacturing techniques.

Figure 3:
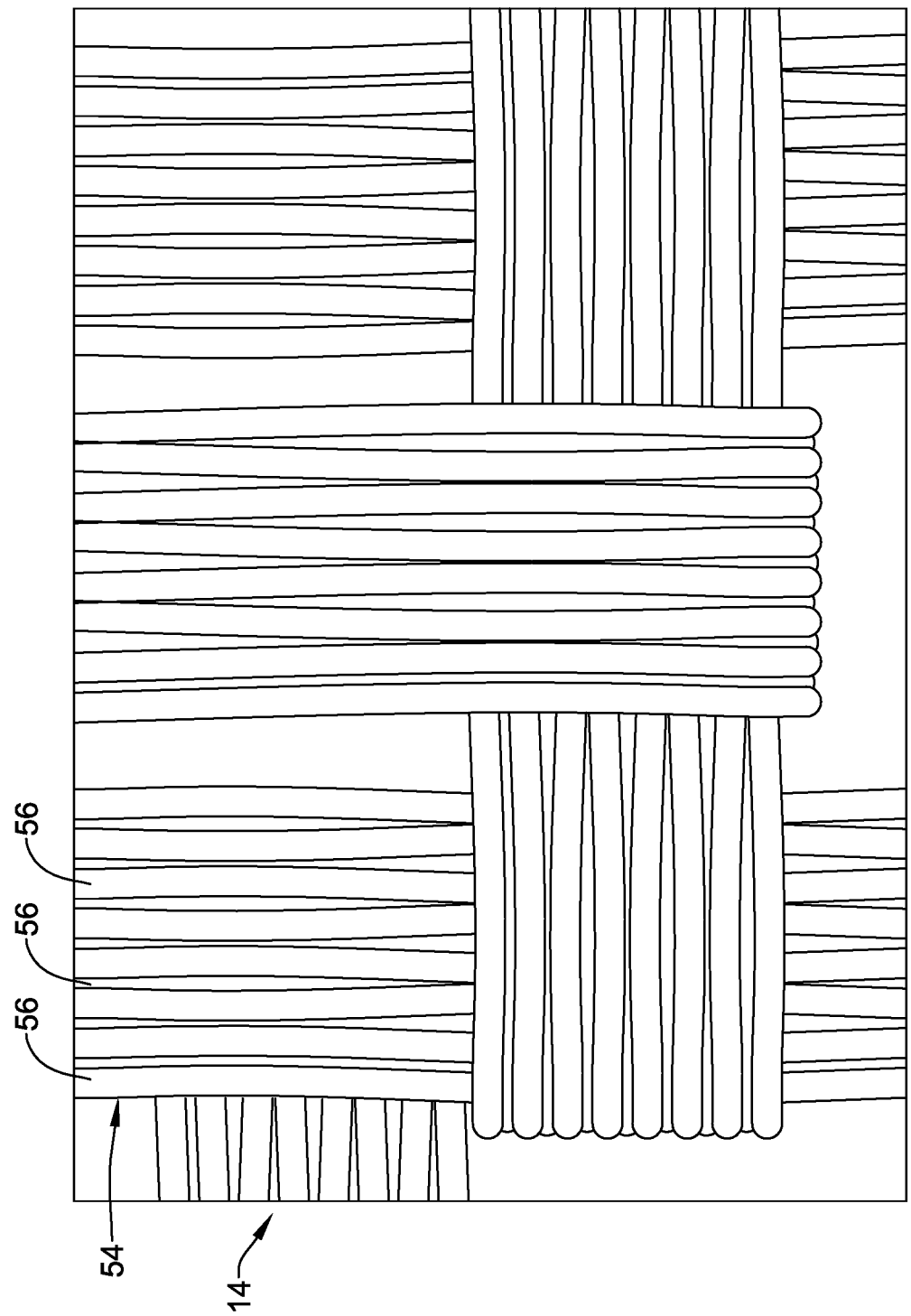
FIG. 3 is a side view of a portion of an example medical device.

As indicated above, the occlusive member 14 may include a woven fabric/material or mesh, a non-woven fabric/material or mesh, a braided and/or knitted material, a fiber, a sheet-like material, a fabric, a mesh, a fabric mesh, a polymeric membrane, a metallic or polymeric mesh, a porous filter-like material, a covering, and/or other suitable construction. The occlusive member 14 may be formed from a suitable material such as polyethylene terephthalate, polyester, nylon, acrylic materials, a polyolefin, and/or the like, combinations thereof, and/or other materials disclosed herein. In other instances, the occlusive material may include metallic mesh formed from nickel-titanium alloy, stainless steel, titanium, other materials disclosed herein, combinations thereof, and/or the like. A portion of the occlusive member 14 is shown in FIG. 3. Here it can be seen that the occlusive member 14 may include one or more bundles of filaments or fibers, which may also be termed fiber bundles 54. The fiber bundles 54 may have a size/diameter in the range of about 10-500 µm, or about 20-200 µm, or about 50-150 µm, or about 100 µm. These are just examples. Other numbers are contemplated. Each of the fiber bundles 54 may include a suitable number of individual filaments 56. For example, each of the fiber bundles 54 may include 2-100 filaments 56, or about 5-50 filaments, or about 5-30 filaments, or about 10-25 filaments, or about 15-20 filaments. These are just examples. Other numbers are contemplated. In some instances, the individual filaments 56 may have a size/diameter in the range of about 1-100 µm, or about 2-25 µm, or about 2-20 µm, or about 5-15 µm, or about 10 µm. These are just examples. Other numbers are contemplated. The one or more fiber bundles 54 may be arranged to form the fabric mesh structure of the occlusive member 14. This may include braiding, knitting, weaving, e-spinning, or otherwise arranging the fiber bundles 54 into the desired arrangement or pattern.

In some instances, the filaments 56 may be surface treated. For example, the filaments can be plasma treated, laser etched, and/or the like. This may improve adhesion of the anti-thrombogenic coating 58 (FIG. 4) and/or increase the surface hydrophobicity (which may improve anti-thrombogenicity), for example by imparting a nanostructure onto the filaments 56, which when coated with a relatively thin anti-thrombogenic coating 58 can lead to a superhydrophobic surface.

Figure 4:
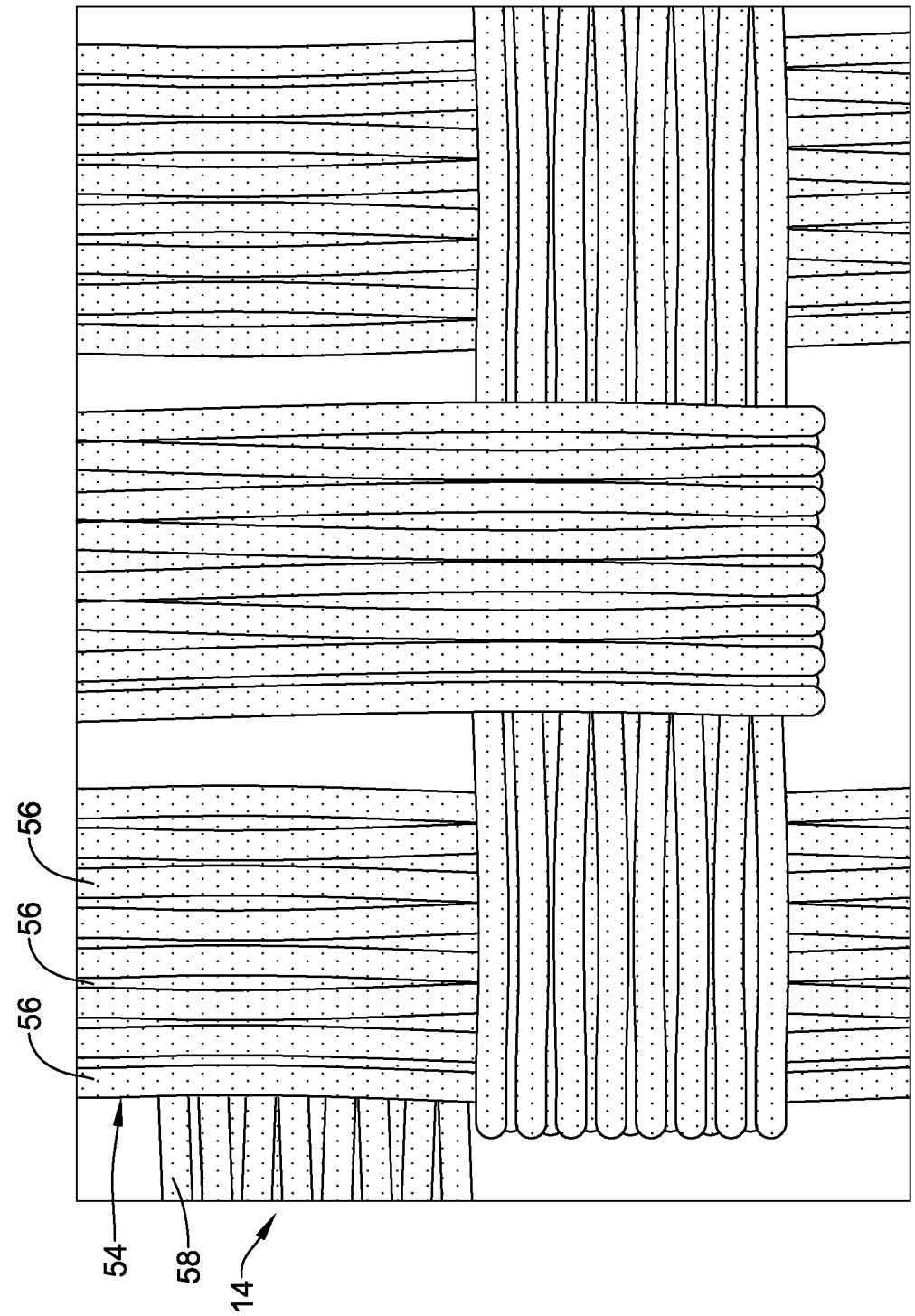
FIG. 4 is a side view of a portion of an example medical device.

As indicated above, the occlusive member 14 may prevent thrombi (i.e. blood clots, etc.) from passing through the occlusive member 14 and out of the left atrial appendage into the blood stream. In some instances, thrombus can form along, for example, the atrial face of the occlusive member 14. In order to reduce formation of thrombus along the occlusive member 14, an anti-thrombogenic coating 58 may be disposed along the occlusive member 14 as shown in FIG. 4. The anti-thrombogenic coating 58 may include a suitable material such as a fluoropolymer, polyvinylidene fluoride, a polyvinylidene fluoride copolymer, poly(vinylidene fluoride-co-hexafluoropropylene), fluorine functional phosphazene polymers, poly[bis (trifluoroethoxy) phosphazene], polytetrafluoroethylene, polytetrafluoroethylene copolymers, combinations thereof, and/or the like.

Figure 5:
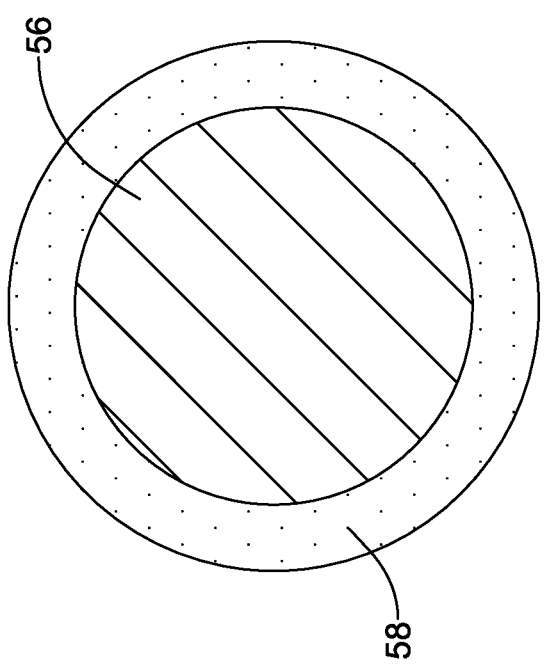
FIG. 5 is a cross-sectional view of a portion of an example medical device.
Figure 6:
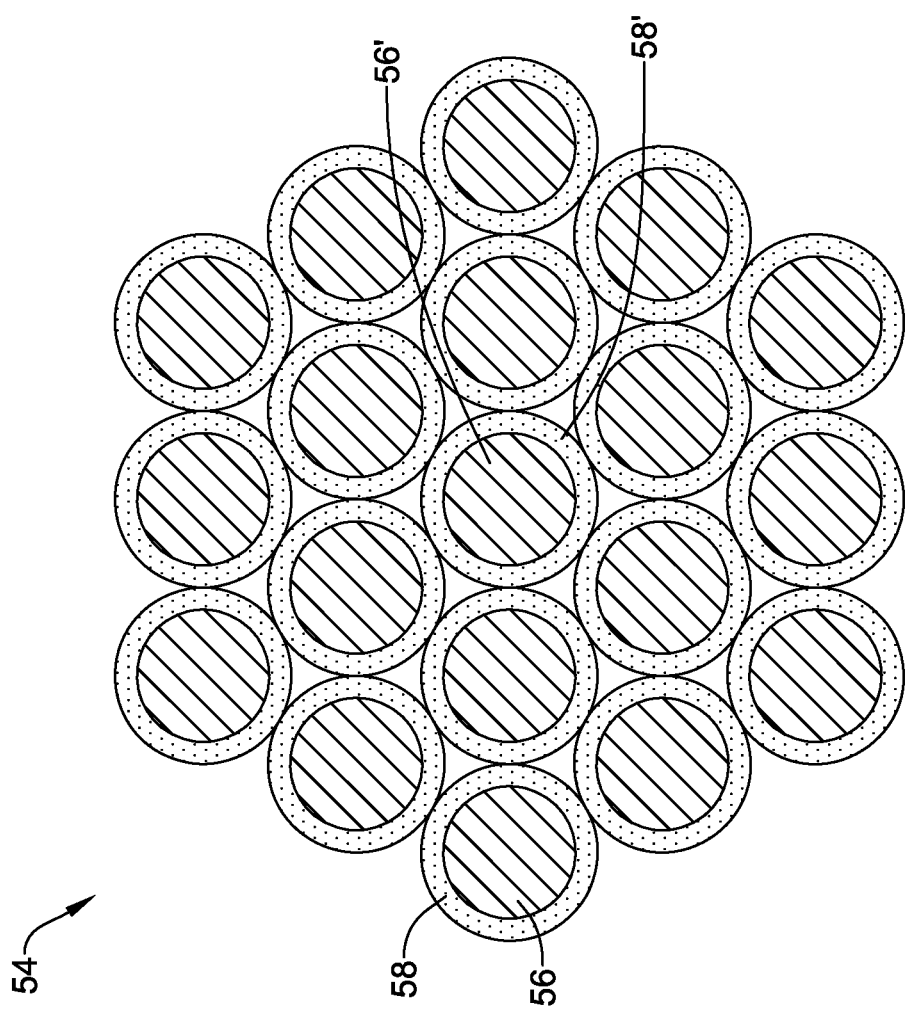
FIG. 6 is a cross-sectional view of a portion of an example medical device.

The anti-thrombogenic coating 58 may be applied to the occlusive member 14 using a suitable method such as dip coating, spray coating, or the like. This may include dissolving the polymer/material for the anti-thrombogenic coating 58 in a suitable solvent to form a dilute solution (e.g., 0.05%-2% solids) and applying (e.g., by dipping, spraying, etc.) the anti-thrombogenic coating 58 to the occlusive member 14. Because of the structure of the occlusive member 14, the anti-thrombogenic coating 58 may efficiently coat throughout the fabric mesh. For example, the anti-thrombogenic coating 58 may wick up throughout the occlusive member 14 (e.g., due to capillary action). When doing so, the anti-thrombogenic coating may cover, surround, and/or otherwise encapsulate each of the filaments 56 of the fiber bundles 54 as depicted in FIG. 5. The anti-thrombogenic coating 58 may be substantially uniform along the occlusive member 14. When the anti-thrombogenic coating 58 is applied via a dip coating process, it would be expected that gravitational forces result in a non-uniform coating thickness. Surprisingly, however, the structure of the occlusive member 14 results in the anti-thrombogenic coating 58 wicking along the filaments 56 and being held in place. Thus, substantially uniform coating thicknesses can be achieved, even when the anti-thrombogenic coating 58 is applied via dip coating. Furthermore, the anti-thrombogenic coating 58 may penetrate between and through the fiber bundles 54. In doing so, the anti-thrombogenic coating 58 may reach an interior region of the fiber bundles 54. For example, FIG. 6 depicts a fiber bundle 54 with an interior filament 56' including the anti-thrombogenic coating 58'.

In some instances, the anti-thrombogenic coating 58 is disposed along only the occlusive member 14. In such instances, the expandable framework 12 may be substantially free of the anti-thrombogenic coating 58. For example, the anti-thrombogenic coating 58 may be applied to the occlusive member 14 prior to the occlusive member 14 being secured to the expandable framework 12. This, however, is not intended to be limiting. In some instances, the anti-thrombogenic coating 58 may be disposed along portions or all of the expandable framework 12. Thus, the expandable framework 12 may include the anti-thrombogenic coating 58. In some instances, the expandable framework 12 may be surface treated (e.g., plasma treated, laser etched, and/or the like). This may improve adhesion of the anti-thrombogenic coating 58 and/or increase the surface hydrophobicity (which may improve anti-thrombogenicity).

Because of the desirable coating/adhesion of the anti-thrombogenic coating 58 to the filaments 56, the integrity of the anti-thrombogenic coating 58 may be relatively high. Should any portions of the anti-thrombogenic coating 58 fail (e.g., become disassociated and/or delaminated from the fiber bundles 54/filaments 56), for example due to loading and/or to repeated deployments), the failure can be limited to along an individual filament 56 rather than the anti-thrombogenic coating 58 as a whole. Because of this, the majority of the occlusive member 14 can maintain its anti-thrombogenic properties even if part of the anti-thrombogenic coating 58 breaches from the occlusive member 14.

The structure of the occlusive member 14 utilizing fiber bundles 54 formed from a plurality of individual filaments 56 may enhance wicking capillary action (e.g., relative to a "monofilament" design) of the anti-thrombogenic coating 58. For example, the increased surface area of the fiber bundles (e.g., due to the filaments 56) may allow the anti-thrombogenic coating 58 to coat, penetrate, and surround/encapsulate the filaments 56. The resulting anti-thrombogenic coating 58 may be relatively thin (e.g., on the order of about 20-200 nm or so) yet covering/surrounding/encapsulating essentially each of the filaments 56 in substantially their entirety. Because the anti-thrombogenic coating 58 is relatively thin, the anti-thrombogenic coating 58 itself may have little or no impact on the mechanical properties of the occlusive member 14.

The materials that can be used for the occlusive implant 10 may include those commonly associated with medical devices. For example, the occlusive implant 10 and/or other components thereof may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the occlusive implant 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the occlusive implant 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the occlusive implant 10 to achieve the same result.

In some embodiments, a degree of Magnetic Resonance Imaging (MRI) compatibility is imparted into the occlusive implant 10. For example, the occlusive implant 10, or portions thereof, may be made of a material that does not substantially distort the image and create substantial artifacts (e.g., gaps in the image). Certain ferromagnetic materials, for example, may not be suitable because they may create artifacts in an MM image. The occlusive implant 10, or portions thereof, may also be made from a material that the MM machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

EXAMPLES

The disclosure may be further clarified by reference to the following Examples, which are prophetic in nature and serve to exemplify some embodiments, and not to limit the disclosure in any way.

Example 1

A 35 mm occlusive implant 10 (e.g., including an expandable framework 12 and an occlusive member 14) was dip coated into a 0.7% solution of poly(vinylidene fluoride-co-hexafluoropropylene) in 90/10 acetone/DMSO. The occlusive implant 10 was allowed to dwell in the coating solution for 20 seconds to allow the coating to penetrate between the filaments 56. The occlusive implant 10 was withdrawn from the coating solution and dried at 120° C. for 1 hour. The coating weight (e.g., of the anti-thrombogenic coating 58) was about 2 mg, which corresponds to a coating thickness of about 50 nm.

The anti-thrombogenic coating 58, for example due to being relatively thin, was not easily visualized. Thus, a visible dye was added to the coating solution. In a separate test, a rectangular piece of fabric mesh material used for the occlusive member 14 was dipped into the coating solution (e.g., the coating solution containing the dye). Only about 1 mm of the fabric mesh contacted to the coating solution. After about 2 seconds, the fabric mesh was removed from the solutions. Surprisingly, the coating on the end of the fabric mesh rapidly migrated up the fabric mesh via strong capillary action to the top of the mesh and could be visualized via the dye. Thus, the coating material was demonstrated to rapidly penetrate and encapsulate the filaments 56 of the occlusive member 14.

Example 2

A 35 mm occlusive implant 10 (e.g., including an expandable framework 12 and an occlusive member 14) was dip coated into a 0.7% solution of poly(vinylidene fluoride-co-hexafluoropropylene) in 90/10 acetone/DMSO as described in Example 1. The occlusive implant was loaded into a deployment sheath and then deployed. The process was repeated a total of twelve times. The occlusive implant 10 was examined by SEM to assess coating damage. Relatively little coating damage was observed and any damage was generally isolated individual filaments.

Example 3

Fifteen millimeter polyethylene terephthalate mesh disks were dip coated in either a 0.7% solution of poly(vinylidene fluoride-co-hexafluoropropylene) or a 1% poly[bis (trifluoroethoxy)phosphazene] solution and then dried. The coated disks were placed in a cup containing heparinized bovine blood, adjusted to an activated clotting time (ACT) of about 220 seconds using protamine. The cups were placed on an orbital shaker incubator at 37° C. and removed at various time points. Any clots forming on the meshes were weighed. It was observed that the coated disks had significantly less clots (e.g., by visualization and/or by weight) than non-coated control disks. For example, Table 1 shows the lower clot weights over time for coated meshes when compared with uncoated control meshes.

TABLE 1

Clot Weight (mg) over Time for Uncoated Versus Coated Meshes

| Time min | Uncoated | Coated |
|---|---|---|
| 10 | 1.85 | 0.02 |
| 15 | 5.63 | 0.3 |
| 20 | 4.98 | 0.23 |
| 25 | 7.75 | 0.97 |
| 32 | 8.65 | 0.65 |
| 65 | 8.3 | 1.9 |

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A left atrial appendage device, comprising:
    an expandable frame configured to shift between a first configuration and an expanded configuration;
    a fabric mesh disposed along at least a portion of the expandable frame;
    an anti-thrombogenic coating disposed along the fabric mesh;
    wherein the fabric mesh includes a plurality of filaments;
    wherein the plurality of filaments are arranged into a fiber bundle; and
    wherein the anti-thrombogenic coating migrates to an interior region of the fiber bundle.

2. The left atrial appendage device of claim 1, wherein the plurality of filaments include polyethylene terephthalate.

3. The left atrial appendage device of claim 1, wherein the plurality of filaments include polyester.

4. The left atrial appendage device of claim 1, wherein the anti-thrombogenic coating encapsulates at least some of the plurality of filaments.

5. The left atrial appendage device of claim 1, wherein the anti-thrombogenic coating individually coats each of the plurality of filaments.

6. The left atrial appendage device of claim 1, wherein the plurality of filaments are arranged in a non-woven configuration.

7. The left atrial appendage device of claim 1, wherein the anti-thrombogenic coating includes a fluoropolymer.

8. The left atrial appendage device of claim 1, wherein the anti-thrombogenic coating includes polyvinylidene fluoride.

9. The left atrial appendage device of claim 1, wherein the anti-thrombogenic coating includes a polyvinylidene fluoride copolymer.

10. The left atrial appendage device of claim 1, wherein the anti-thrombogenic coating includes poly(vinylidene fluoride-co-hexafluoropropylene).

11. The left atrial appendage device of claim 1, wherein the anti-thrombogenic coating includes poly[bis (trifluoroethoxy)phosphazene].

12. A left atrial appendage device, comprising: an expandable framework configured to shift between a delivery configuration and a deployed configuration; wherein the expandable framework is configured to engage a left atrial appendage when in the deployed configuration; a fabric disposed along at least a portion of the expandable framework, the fabric including one or more knitted fiber bundles; wherein each of the one or more knitted fiber bundles include a plurality of filaments; and an anti-thrombogenic coating disposed along each of the plurality of filaments that migrates to an interior region of the knitted fiber bundle.

13. The left atrial appendage device of claim 12, wherein the anti-thrombogenic coating encapsulates each of the plurality of filaments.

14. The left atrial appendage device of claim 12, wherein the anti-thrombogenic coating includes a fluoropolymer.

15. The left atrial appendage device of claim 12, wherein the anti-thrombogenic coating includes poly(vinylidene fluoride-co-hexafluoropropylene).

16. An occlusive medical device, comprising: an expandable frame configured to shift between a delivery configuration and an expanded configuration; wherein the expandable frame is configured to be implanted adjacent to a left atrial appendage; a fabric mesh disposed along at least a portion of the expandable frame, the fabric mesh including one or more fiber bundles arranged into a pattern; wherein each of the one or more fiber bundles include a plurality of filaments; an anti-thrombogenic coating disposed along each of the plurality of filaments that migrates to an interior region of the one or more fiber bundles; and wherein at least one of the one or more fiber bundles includes an interior region and wherein a section of the anti-thrombogenic coating is disposed along the interior region.

17. The occlusive medical device of claim 16, wherein the anti-thrombogenic coating encapsulates each of the plurality of filaments.

* * * * *